(12) United States Patent
Cullen et al.

(10) Patent No.: US 6,365,772 B1
(45) Date of Patent: Apr. 2, 2002

(54) FACILE SYNTHESIS OF PHOSPHONOMETHYLGLYCINE FROM PHOSPHONOMETHYLIMINODIACETIC ACID

(75) Inventors: Barry A. Cullen, Lyndeboro; Brian A. Parker, Nashua, both of NH (US)

(73) Assignee: Hampshire Chemical Corp., Nashua, NH (US)

( * ) Notice: Subject to any disclaimer, the term of this patent is extended or adjusted under 35 U.S.C. 154(b) by 0 days.

(21) Appl. No.: 08/453,003

(22) Filed: May 30, 1995

(51) Int. Cl.[7] ................................................ C07F 9/22
(52) U.S. Cl. ........................................................ 562/17
(58) Field of Search ............................................. 562/17

(56) References Cited

U.S. PATENT DOCUMENTS

| | | | |
|---|---|---|---|
| 3,950,402 A | 4/1976 | Franz | 260/502.5 |
| 3,954,848 A | 5/1976 | Franz | 260/502.5 |
| 3,969,398 A | 7/1976 | Hershman | 260/502.5 |
| 4,002,672 A | 1/1977 | Smith | 260/502.5 |
| 4,147,719 A | 4/1979 | Franz | 260/501.12 |
| 4,579,689 A | 4/1986 | Hershamn et al. | 260/502.5 |
| 4,582,650 A | 4/1986 | Felthouse | 260/502.5 |
| 4,696,772 A | 9/1987 | Chou | 260/502.5 |
| 4,724,103 A | 2/1988 | Gentilcore | 260/502.5 |
| 4,775,498 A | 10/1988 | Gentilcore | 260/502.5 |
| 4,898,972 A | 2/1990 | Fields, Jr. et al. | 562/17 |

*Primary Examiner*—Michael L. Shippen

(57) ABSTRACT

A process for the preparation of phosphonomethylglycine in nearly quantitative yields which eliminates the use of a noble metal co-catalyst and its concomitant problems. The oxygen-containing gas is replaced with the much more chemically active hydrogen peroxide, which in combination with activated carbon, oxidizes the PMIDA to PMG in very high yield. The amount of oxidant allowed to react with PMIDA is a function of the concentration of oxygen in the gaseous reaction products, and is controlled by monitoring that concentration. In another embodiment, the oxidizing agent is an oxygen-containing gas. In either case, the concentration of oxygen in the gaseous reaction product is monitored to determine the end point of the reaction.

22 Claims, 2 Drawing Sheets

Typical oxidation of PMIDA acid with H2O2 and activated carbon

FACILE SYNTHESIS OF PHOSPHONOMETHYLGLYCINE FROM PHOSPHONOMETHYLIMINODIACETIC ACID

BACKGROUND OF THE INVENTION

The present invention relates to N-phosphonomethyliminodiacetic acid ("PMIDA") of the formula (I):

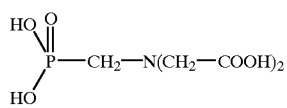

(I)

and to N-phosphonomethylglycine. Compound I is an important intermediate in the formation of N-phosphonomethylglycine ("glyphosate"), which is a translocated, postemergence, broad spectrum herbicide.

Glyphosate has heretofore been prepared by a variety of oxidations of PMIDA. For example, U.S. Pat. No. 3,954,848 discloses the production of glyphosate by the acid catalyzed oxidation-hydrolysis of PMIDA. Specifically, PMIDA is mixed with water and an acid and is heated to an elevated temperature. An oxidizing agent such as hydrogen peroxide is then added to convert the PMIDA to glyphosate, which is then isolated by precipitation. U.S. Pat. No. 3,969,398 discloses the oxidation of PMIDA to glyphosate employing a molecular oxygen-containing gas such as air, oxygen, oxygen diluted with helium, argon nitrogen or other inert gases, oxygen-hydrocarbon mixtures, etc., and employing activated carbon as the catalyst. U.S. Pat. No. 4,147,719 discloses the production of certain mono- and di-salts of glyphosate in a single aqueous reaction system by oxidizing a salt of PMIDA with a molecular oxygen-containing gas in the presence of platinum supported on an activated carbon substrate. The oxidation reaction is conducted at superatmospheric pressures in the range of 1.5 to 5 $kg/cm^2$ or higher. U.S. Pat. No. 4,898,972 discloses the production of glyphosate by the oxidation of PMIDA using a salt of cobalt or manganese in the presence of bromide ions. U.S. Pat. No. 4,002,672 discloses the production of glyphosate and salts thereof by the acid catalyzed hydrolysis of PMIDA. PMIDA is contacted with a strong acid having a pKa of less than 2.2, at an elevated temperature so as to cause the decomposition or hydrolysis of the phosphonomethyl iminodiacetic acid into N-phosphonomethyl-glycine and other decomposition products. U.S. Pat. No. 3,954,898 discloses how a large variety of oxidizing agents, including hydrogen peroxide, can be used to oxidize PMIDA to glyphosate in the presence of acetic or stronger acid, at 70–100° C. U.S. Pat. No. 4,696,772 discloses how the activity of the activated carbon catalyst can be enhanced by first removing oxides of carbon from the surface of the carbon.

As can be seen from the foregoing, phosphonomethylglycine can be made by oxidizing phosphonomethyliminodiacetic acid by a myriad of techniques. However, all but a few of these produce an effluent that contains formaldehyde and toxic metals and/or strong acids. The use of very strong acid solutions at elevated temperatures necessitates the use of corrosion resistance equipment. Moreover, some of these processes must be run under very dilute conditions, requiring large amounts of energy to concentrate the solutions to allow the glyphosate product to be recovered in an economically attractive yield.

Phosphonomethylglycine also may be prepared by oxidizing PMIDA with an oxygen-containing gas in the presence of a noble metal co-catalyst for oxidizing by-product formaldehyde or formic acid. Oxidation of PMIDA in the presence of the noble metal but in the absence of activated carbon does not produce any product, see U.S. Pat. No. 3,950,402. The drawback to the noble metal catalysts is that they are very expensive and must be protected from rapid amine deactivation by either coating them with a polymer as disclosed in U.S. Pat. No. 4,579,689, or encapsulating them in a microcrystalline inorganic matrix, as disclosed in U.S. Pat. No. 4,582,650.

In accordance with U.S. Pat. No. 4,147,719, PMG salts may be prepared directly from a salt of PMIDA using an oxygen-containing gas in the presence of a noble metal oxidation catalyst, namely, platinum, supported on an activated carbon substrate. Again, though conversions are high, so is the cost of the catalyst. Thus, extreme care must be taken not to lose any catalyst during work-up of the product. The use of the noble metal catalyst is said to provide concurrent oxidation of the formaldehyde co-product as it is formed, which significantly reduces the time and expense otherwise required to remove this co-product from the final reaction product. The '719 patent teaches that activated carbon catalysts alone do not provide for this concurrent oxidation of formaldehyde, and in fact cause increased production of undesirable by-products.

It is therefore an object of the present invention to provide a process for preparing phosphonomethylglycine that eliminates the drawbacks of the prior art processes.

It is a more specific object of the present invention to provide a process for preparing phosphonomethylglycine that eliminates the deleterious effluent and minimizes the cost of the catalyst.

SUMMARY OF THE INVENTION

The problems of the prior art have been overcome by the present invention, which provides a process for the preparation of phosphonomethylglycine in nearly quantitative yields, while simultaneously oxidizing the toxic by-product formaldehyde to formic acid and $CO_2$ or salts thereof. In general terms, the process of the present invention eliminates the use of the noble metal co-catalyst and its concomitant problems. The oxygen-containing gas is replaced with the much more chemically active hydrogen peroxide, which in combination with activated carbon, oxidizes the PMIDA to PMG in very high yield, and oxidizes formaldehyde by-product to formate and $CO_2$, leaving a no-longer toxic effluent that can be readily biodegraded. The rate of oxidant addition is carefully controlled and monitored.

DETAILED DESCRIPTION OF THE INVENTION

Figure 1:
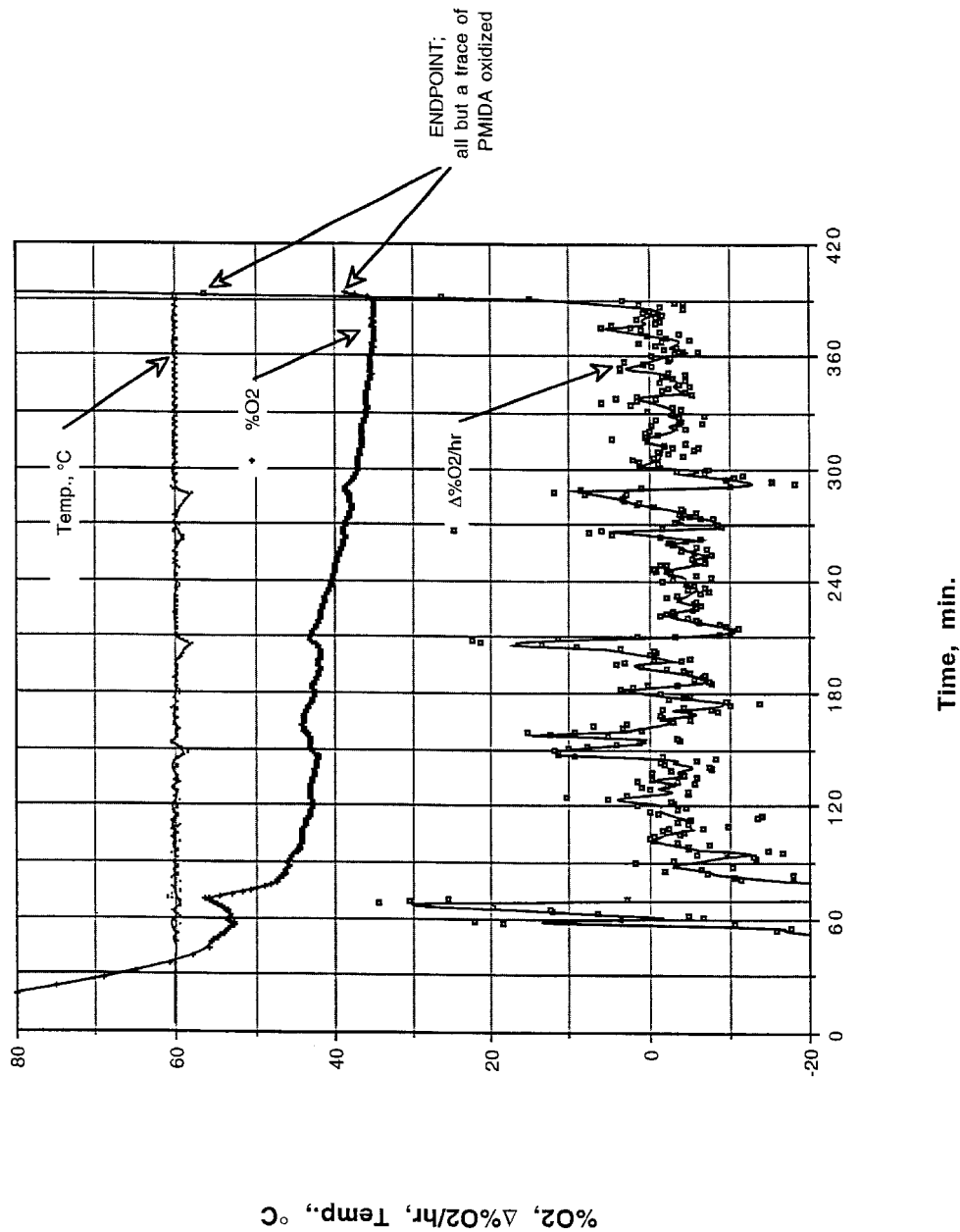
FIG. 1 is a graph of a typical oxidation of PMIDA with hydrogen peroxide and activated carbon.

The starting material, PMIDA, can be prepared by conventional methods well known to those skilled in the art, such as by the reaction of formaldehyde, iminodiacetic acid and orthophosphorous acid in the presence of a strong acid such as hydrochloric or sulfuric acid. The resulting N-phosphonomethyl-iminodiacetic acid mixture can be used directly in the instant process, or the N-phosphonomethyliminodiacetic acid can be isolated from the reaction mixture prior to use as a starting material in the instant process.

The oxidizing agent in accordance with the present invention can be an inorganic peroxide, preferably hydrogen peroxide, or a oxygen-containing gas, such as air, pure oxygen, ozone, etc. In one embodiment of the invention, the oxygen-containing gas is used to oxidize most of the PMIDA, and then peroxide is used to complete the reaction. More specifically, since oxygen-containing gases suitable for use in the present invention are generally less expensive than peroxide, about 60–90% of the oxidation of PMIDA, preferably about 70–80% of the oxidation of PMIDA, can be carried out using the oxygen-containing gas. Thereafter, peroxide can be used to complete the oxidation of the PMIDA and to oxidize formaldehyde generated. Adding peroxide after about 90% of the PMIDA has been oxidized by the oxygen-containing gas is not desirable, since the presence of unreacted PMIDA seems to protect against the oxidation of PMG by the peroxide. The exact point at which peroxide is used will therefore depend upon a balance between the cost savings achieved by using the oxygen-containing gas and the tolerable amount of deleterious oxidation of PMG by the peroxide. Preferably the amount of oxidizing agent used is regulated so as to maintain the concentration of oxygen in the vent gases at less than about 10%, more preferably less than about 3%.

The activated carbon catalysts employed in the instant invention are commercially available, and include NORIT SX+ and RO 0.8, DARCO KB, CALGON RB, RD, CAL, CPG and BL catalysts, for example. Either granular or powdered activated carbon is suitable. The activated carbon should have a specific surface area of from 100 to 2000 $m^2/g$, preferably about 400 to about 1600 $m^2/g$. The amount of activated carbon used can range from about 0.1 unit/PMIDA to greater than about 10 units/PMIDA, as would occur in a packed continuous reactor. For a batch reaction, the preferred ratio of carbon to PMIDA ranges from about 0.2 to about 0.4.

Surprisingly, the inventors of the present invention have found that if the feed rate of $H_2O_2$ to the reaction mix is continuously regulated so as to maintain the % $O_2$ in the vent gases at a low level, such as less than about 10%, preferably less than about 3%, then the decomposition of the $H_2O_2$ by the activated carbon, to $O_2$ and $H_2O$, becomes merely an insignificant side reaction, although those skilled in the art know that the oxygen in the vent gas could be controlled at a higher concentration (such as 50% or 20%) with a corresponding increase in raw material costs. Controlling the oxidation by continuously measuring the concentration $O_2$ in the vent gases allows the efficiency of the reaction to be maximized. Surprisingly, the inventors have also discovered that not only is the rate of oxidation of co-product $CH_2O$ faster than the oxidation of PMIDA at all conditions studied, but the concentration of $O_2$ rapidly increases by much greater than 5% at the time when all of the PMIDA has been consumed. This has been confirmed by HPLC analysis, and allows the reaction to be stopped when the conversion of PMIDA to PMG is at a maximum and the undesirable oxidation of PMG is at a minimum. For example, the reaction can be stopped when the oxygen concentration increases at a rate exceeding about 20% per hour.

Preferably the oxidation is carried out at a temperature of from about 30° C. to about just below the boil, most preferably at from about 50° C. to about 65° C. At higher temperatures, formic acid by-product tends to react with glyphosate product, yielding water soluble N-formyl-glyphosate (HCO-PMG), which in turn can be oxidized to N-formyl-aminomethylphosphonic acid. By operating at lower temperatures, the rate of HCO-PMG formation is reduced faster than the rate of oxidation. The reaction temperature and the concentration of activated carbon should be chosen so as to provide a short reaction time and minimize the formation of HCO-PMG.

The concentration of the phosphonomethyliminodiacetic acid should be from about 1% to about 60% or higher in water. Preferably the concentration is about 35% to about 55%.

Salts of PMG can be prepared by using the appropriate salt of N-phosphonomethyliminodiacetic acid as the starting material. Suitable salt forming cations include alkali metals, alkaline earth metals, trimethylsulfonium, guanidinium, urea, ammonium and organic ammonium (provided that when the organic group is aryl, the ammonium salt is a primary amine salt) including those prepared from organic amines such as alkyl amines, alkylene amines and alkanol amines containing not more than 2 amine groups, such as methylamine, ethylamine, n-propylamine, isopropylamine, n-butylamine, isobutylamine, sec-butylamine, n-amylamine, isoamylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoanylamine, dihexylamine, di-heptylamine, dioctylamine, trimethylamine, triethylamine, tri-n-propylamine, triisopropylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, di-butenyl-2-amine, n-hexenyl-2-amine and propylenediamine; primary aryl amines such as aniline, methoxyaniline, ethoxyaniline, o,m,p-toluidine, phenylenediamine, 2,4,6-tribromoanaline, benzidine, napthylamine, o,m,p-chloroaniline, and the like; and heterocyclic amines such as pyridine, morpholine, piperidine, pyrrolidine, indoline, azepine and the like.

The instant invention will be better understood by reference to the following specific but non-limiting examples. It is understood that said invention is not limited by these procedures which are offered merely as illustrations; modifications can be made without departing from the spirit and scope of the invention.

EXAMPLE 1

A slurry of PMIDA acid (0.375 M) was reacted with 0.56 M of 28% ammonia to give a 25% slurry of PMIDA acid equivalent, as an equimolar mixture of the mono- and di-ammonium salts. To this was added 40 grams of activated carbon (Calgon type RB pulverized) and the slurry was rapidly stirred. A 10.2% solution of $H_2O_2$ was then pumped into the slurry at a rate of 0.575 g./min. until a total of about 2.3 M has been added. The temperature was maintained between 25° and 30° C. during the reaction by immersing the reaction flask in an unheated or cooled water bath during the addition. Periodically, samples were withdrawn, filtered to remove solids and analyzed by HPLC. Surprisingly, no formaldehyde or any other impurities normally found when oxygen is used in place of $H_2O_2$ were found, especially towards the end of the addition where little PMIDA remains to be oxidized. Only PMG, a small amount of formic acid and a trace of N-formyl-PMG were found.

EXAMPLE 2

The reaction of Example 1 was repeated, except that the mono-isopropylamine salt of PMIDA was used as the starting reactant, and 25% $H_2O_2$ was used. Essentially the same results were obtained.

EXAMPLE 3

The reaction of Example 1 was repeated, except that the tri-sodium salt of PMIDA was used as the starting reactant, and 50% $H_2O_2$ was used. The tri-sodium salt did not oxidize as readily as the lower salts.

EXAMPLE 4

A 500 ml. Parr pressure bottle was charged with water plus PMIDA (0.375 M) plus, when required, a quantity of base, and activated carbon (granular or powder). The contents were stirred with a magnetic stirrer and heated to and maintained at the desired reaction temperature with an electric heating tape. When required, the bottle was pressurized and maintained at the desired pressure with a back-pressure control valve; otherwise the bottle was vented to atmosphere. The vent gases from the reactor were continuously monitored for % $O_2$ and the reaction conditions recorded every minute. Table 1 lists the operating conditions for each of the 42 experiments.

Typically the % $O_2$ in the vent gases was below 10% for the lower reaction temperatures, and when the reaction temperature was raised to $\geq 60°$ C., the vent gas contained essentially no free $O_2$. When approximately 2 equivalents of $H_2O_2$ had been added, the % $O_2$ increased rapidly, indicating the reaction to PMG to be complete. This was confirmed by HPLC analysis of the samples. Table 2 lists the results of the 42 experiments. FIG. 1 shows a graph of a typical oxidation.

TABLE 1

| EXPERIMENT | % PMIDA | g PMIDA/ g C | Carbon Type | M base/ M PMIDA | Base Type | Temp., ° C. | Press., psig | M H2O2/ M PMIDA | % H2O2 | ≈M H2O2/min./ M PMIDA |
|---|---|---|---|---|---|---|---|---|---|---|
| 1 | 25.8 | 2.13 | Calgon RB Pulv. | 1.49 | NH3 | ≈30 | | 1.58 | 10.2 | 0.0110 |
| 2 | 25.0 | 2.13 | Calgon RB Pulv. | 1.00 | i-Pr-amine | ≈30 | | 2.49 | 25.0 | 0.0098 |
| 3 | 25.0 | 2.13 | Calgon RB Pulv. | | | ≈30 | | 2.00 | 50.0 | |
| 4 | 25.0 | 2.13 | Calgon RB Pulv. | | | ≈30 | | 2.62 | 50.0 | 0.0215 |
| 5 | 25.0 | 2.13 | Calgon RB Pulv. | 1.00 | NH3 | 40 | 37.5 | 2.40 | 50.0 | 0.0150 |
| 6 | 25.0 | 2.13 | Calgon RB Pulv. | 3.00 | NaOH | 40 | 37.5 | 2.82 | 50.0 | 0.0130 |
| 7 | 25.0 | 2.13 | Calgon RB Pulv. | 2.00 | NaOH | 40 | 37.5 | ≈2.4 | 50.0 | 0.0130 |
| 8 | 25.0 | 2.13 | Calgon RB Pulv. | 1.85 | NH3 | 60 | 37.5 | 1.84 | 50.0 | 0.0168 |
| 9 | 25.0 | 2.13 | Calgon RB Pulv. | 1.00 | i-Pr-amine | 60 | 37.5 | 2.00 | 50.0 | 0.0175 |
| 10 | 25.0 | 2.13 | Calgon RB Pulv. | | | 60 | 37.5 | 2.00 | 50.0 | 0.0171 |
| 11 | 25.0 | 2.13 | Calgon RB Pulv. | | | 60 | | 2.09 | 50.0 | 0.0171 |
| 12 | 25.0 | 2.13 | Calgon RB Pulv. | | | 45 | | 2.31 | 50.0 | 0.0139 |
| 13 | 25.0 | 2.13 | Calgon RB Pulv. | | | 75 | | 2.04 | 50.0 | 0.0163 |
| 14 | 25.0 | 2.84 | Calgon RB Pulv. | | | 60 | | 2.04 | 50.0 | 0.0171 |
| 15 | 25.0 | 4.26 | Calgon RB Pulv. | | | 60 | | 2.04 | 50.0 | 0.0163 |
| 16 | 25.0 | 8.52 | Calgon RB Pulv. | | | 60 | | 2.09 | 50.0 | 0.0131 |
| 17 | 25.0 | 8.52 | Norit A Supra | | | 60 | | 2.04 | 50.0 | 0.0118 |
| 18 | 25.0 | 17.40 | Norit A Supra | | | 75 | | 2.04 | 50.0 | 0.0093 |
| 19 | 25.0 | 17.40 | Calgon RB Pulv. | | | 75 | | 2.04 | 50.0 | 0.0087 |
| 20 | 25.0 | 17.40 | Norit SX Plus | | | 75 | | 2.04 | 50.0 | 0.0092 |
| 21 | 43.6 | 8.52 | Calgon RB Pulv. | | | 60 | | 2.04 | 50.0 | 0.0092 |
| 22 | 25.0 | 2.13 | Calgon RB Pulv. | 1.00 | i-Pr-amine | 60 | | 2.04 | 50.0 | 0.0085 |
| 23 | 25.0 | 2.13 | Calgon RB Pulv. | 1.00 | i-Pr-amine | 60 | | 2.04 | 50.0 | 0.0093 |
| 24 | 25.0 | 2.13 | Calgon RB Pulv. | 1.00 | i-Pr-amine | 75 | | 2.04 | 50.0 | 0.0093 |
| 25 | 25.0 | 2.13 | Calgon RB Pulv. | 1.00 | i-Pr-amine | 45 | | 2.04 | 50.0 | 0.0044 |
| 26 | 25.0 | 8.52 | Calgon RB Pulv. | 1.00 | i-Pr-amine | 60 | | 2.04 | 50.0 | 0.0040 |
| 27 | 25.0 | 3.40 | Calgon RB Pulv. | 1.00 | i-Pr-amine | 60 | | 2.04 | 50.0 | 0.0081 |
| 28 | 25.0 | 2.13 | Calgon RB Pulv. | 1.00 | i-Pr-amine | 60 | | 2.04 | 50.0 | 0.0107 |
| 29 | 25.0 | 2.13 | Calgon RB Pulv. | 1.00 | i-Pr-amine | 90 | | 2.04 | 50.0 | 0.0118 |
| 30 | 25.0 | 2.13 | Calgon RB Pulv. | | | 60 | 37.5 | 2.04 | 50.0 | 0.0055 |
| 31 | 25.0 | 2.13 | Calgon RB Pulv. | 1.00 | i-Pr-amine | 60 | | 2.04 | 50.0 | 0.0109 |
| 32 | 25.0 | 2.13 | Calgon CPG 12 × 40 | 1.00 | i-Pr-amine | 60 | | 2.04 | 50.0 | 0.0091 |
| 33 | 25.0 | 2.13 | Calgon CPG 12 × 40 | | | 60 | | 2.04 | 50.0 | 0.0094 |
| 34 | 25.0 | 2.13 | Calgon RB Pulv. | 1.00 | i-Pr-amine | 60 | | 2.04 | 50.0 | 0.0094 |
| 35 | 25.0 | 2.13 | Calgon RB Pulv. | | | 60 | | 2.04 | 50.0 | 0.0111 |
| 36 | 25.0 | 2.13 | Calgon CPG 12 × 40 | 1.00 | i-Pr-amine | 60 | | 2.04 | 50.0 | 0.0970 |
| 37 | 25.0 | 2.13 | Calgon RB Pulv. | 1.00 | i-Pr-amine | 60 | | 2.04 | 50.0 | 0.1150 |
| 38 | 25.0 | 2.13 | Calgon RB Pulv. | 1.00 | i-Pr-amine | 60 | | 2.04 | 50.0 | 0.0103 |
| 39 | 25.0 | 2.13 | Calgon CPG 12 × 40 | 1.00 | i-Pr-amine | 60 | | 2.04 | 50.0 | 0.0091 |
| 40 | 25.0 | 2.13 | Calgon RB Pulv. | 1.00 | i-Pr-amine | 60 | | 2.04 | 50.0 | 0.0115 |
| 41 | 25.0 | 2.13 | Calgon RB Pulv. | 1.00 | i-Pr-amine | 60 | | 2.04 | 50.0 | 0.0107 |
| 42 | 25.0 | 2.13 | Calgon RB Pulv. | 1.00 | i-Pr-amine | 60 | | 2.04 | 50.0 | 0.0115 |

TABLE 2

| EXPERIMENT | % MeAMPA | % AMPA | % IDA | % MePMG | % PMG | % PMIDA | % HCO-MeAMPA | % HCO-AMPA | % HCO2H | % HCO-PMG | % conv to PMG | % in hand yield |
|---|---|---|---|---|---|---|---|---|---|---|---|---|
| 1 | | | | | 8.6 | 2.67 | | | 1.98 | 0.20 | | |
| 2 | | | | | 10.5 | | | 0.10 | 2.34 | 0.27 | | |
| 3 | | | | | | | | | | | | |
| 4 | | 0.18 | | 0.33 | 3.7 | ≈0.24 | | | 3.35 | 0.04 | | |
| 5 | | 0.17 | 0.08 | | 16.0 | ≈0.7 | | 0.02 | 3.81 | 0.36 | | |
| 6 | | | | | 11.7 | ≈6 | | 0.75 | 3.63 | 0.23 | | |
| 7 | | | trace | | 13.2 | ≈3.6 | | 0.09 | 3.43 | 0.16 | | |
| 8 | | | trace | | 16.7 | ≈0.2 | | 0.22 | 2.71 | 0.33 | | |
| 9 | | 0.28 | trace | ≈0.2 | 16.0 | | | 0.09 | 3.78 | 0.78 | | |
| 10 | | | | 0.33 | 1.1 | | | | 3.09 | 0.14 | 97.9 | 87.0 |
| 11 | | | | 0.20 | 1.1 | | | | 3.21 | 0.14 | 98.5 | 90.7 |
| 12 | | | | 0.34 | 1.1 | | | | 3.62 | 0.10 | 98.2 | 90.2 |
| 13 | | | | | | | | | | | | 87.7 |
| 14 | | | | 0.40 | 0.9 | | | | 3.94 | 0.06 | 98.0 | 88.6 |
| 15 | | | | 0.36 | | | | | 3.74 | 0.06 | 98.2 | 94.0 |
| 16 | | 0.14 | trace | | 1.0 | 0.40 | | 0.51 | 3.10 | 0.38 | 93.6 | 83.7 |
| 17 | 0.12 | 0.16 | | | 1.3 | 0.20 | | 1.00 | 1.94 | 0.28 | 91.7 | 90.0 |
| 18 | | | | | | | | | | | 99.2 | 57.9 |
| 19 | | | | | | | | | | | | 64.5 |
| 20 | | | | | | | | | | | | 64.3 |
| 21 | | | | | 1.4 | 0.40 | | 0.29 | 7.90 | 1.30 | 89.5 | 80.6 |
| 22 | | | | | 7.6 | 0.19 | 0.32 | 0.57 | 2.80 | 1.30 | 87.8 | |
| 23 | | | | | 7.7 | 0.61 | 0.34 | 0.57 | 3.11 | 0.92 | 87.7 | |
| 24 | | 0.23 | | | 7.4 | 0.57 | 0.31 | 1.15 | 1.94 | | 87.3 | |
| 25 | | | | | 12.6 | 2.44 | 0.36 | 0.32 | 2.93 | 0.43 | 81.6 | 80.9 |
| 26 | 0.47 | | | | 11.1 | 1.32 | | 1.82 | 3.49 | | 82.7 | 65.0 |
| 27 | 0.09 | | | | 13.8 | 0.87 | 0.36 | 0.98 | 3.38 | 0.95 | 80.3 | 78.8 |
| 28 | 0.34 | | | | 7.9 | 0.48 | 0.49 | 2.57 | 4.00 | 3.50 | 76.2 | 28.8 |
| 29 | 0.47 | | | | 10.9 | 1.20 | 0.38 | 1.78 | 3.29 | 2.54 | 70.2 | 57.4 |
| 30 | 0.05 | | | | 13.4 | | | 0.05 | 0.68 | 0.32 | 95.7 | 61.7 |
| 31 | | | | | 13.6 | | 0.36 | 0.55 | 3.20 | 0.83 | 90.4 | 77.6 |
| 32 | | | | | 13.6 | | 0.32 | 1.80 | 3.00 | 1.04 | 82.6 | 76.6 |
| 33 | 0.32 | | | | 0.9 | | 0.02 | | 3.90 | 0.50 | 97.8 | 5.0 |
| 34 | 0.68 | 0.88 | | | 4.9 | 0.69 | 0.06 | | 4.00 | 0.70 | 81.4 | 31.6 |
| 35 | | 0.39 | | | 12.5 | | 0.33 | | 3.50 | 0.75 | | 80.0 |
| 36 | 0.55 | 0.79 | | | 8.3 | | 0.02 | | 3.09 | 0.29 | 92.6 | 42.5 |
| 37 | | 0.87 | | | 13.5 | | 0.34 | | 3.55 | 1.01 | | 88.0 |
| 38 | 0.85 | | | | 13.4 | | 0.23 | | 3.58 | 0.89 | 94.0 | 86.9 |
| 39 | 0.26 | 0.45 | 0.04 | 0.30 | 1.7 | | | 0.07 | 3.61 | 0.62 | 86.1 | 8.9 |
| 40 | | 1.07 | | | 13.8 | | 0.24 | 0.20 | 3.76 | 1.13 | | 88.7 |
| 41 | | 0.86 | | | 14.2 | | 0.46 | 1.08 | 3.45 | 1.90 | | 89.8 |
| 42 | | 1.56 | | | 13.1 | | 0.44 | 1.05 | 3.21 | 1.62 | | 84.7 |

EXAMPLE 5

A 500 ml Parr pressure bottle equipped with a sintered stainless steel (s.s.) sparge tube for $O_2$ dispersion, a similar tube for sampling, a magnetic stirrer, a ⅛" s.s. 100 Ω DIN Pt RTD, a s.s. air condenser topped with a pressure relief valve set at 60 psi, a pressure gauge, a vent valve and an adjustable back-pressure control valve. The bottle was charged with 200 g $H_2O$, 160 g PMIDA and 40 g Norit SX+ activated carbon.

Figure 2:
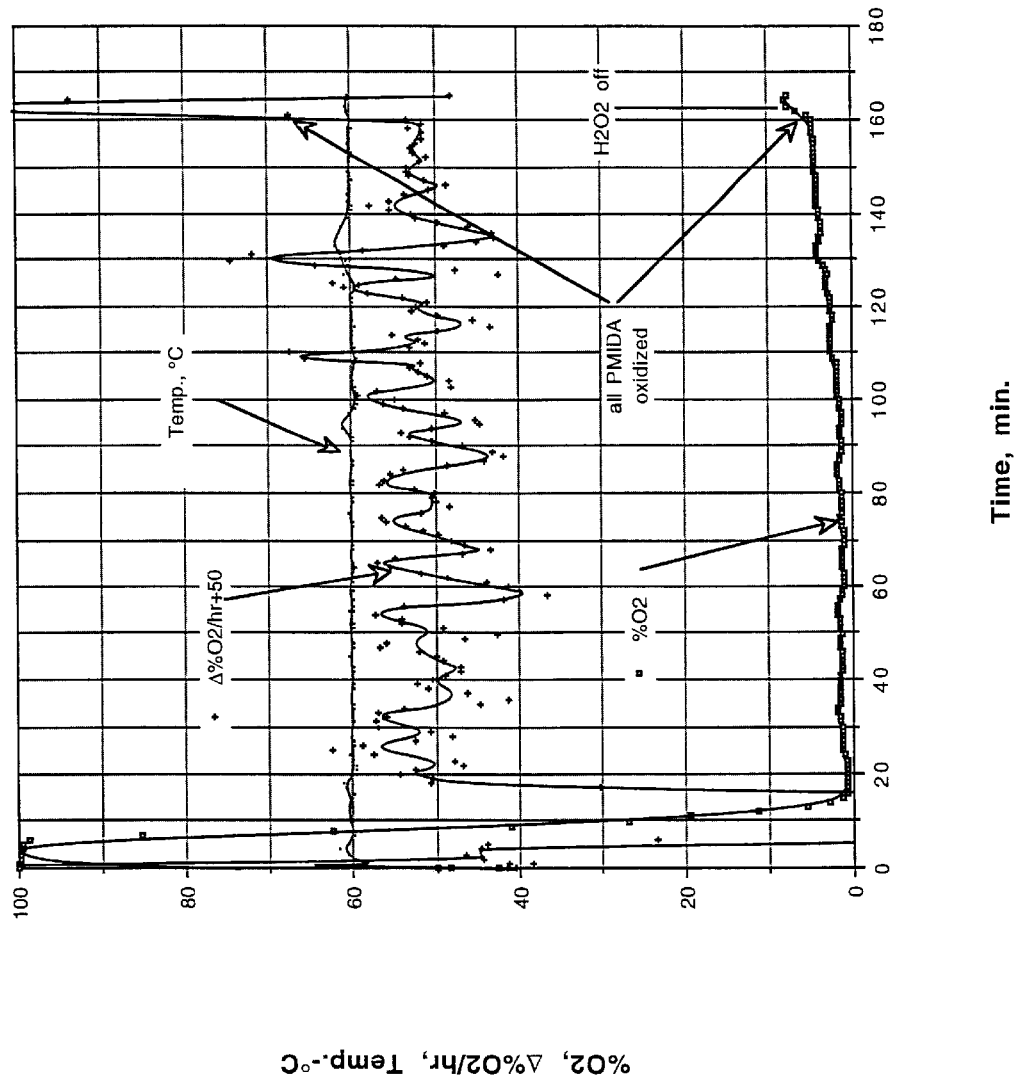
FIG. 2 is a graph of an oxidation of PMIDA in accordance with Example 5.

The vessel was heated and maintained at 60° C. with an electric mantle and the temperature controlled by a Macintosh II running Workbench™. A Microelectrodes, Inc. oxygen probe and meter were used to monitor the concentration of $O_2$ in the vent gases from the back-pressure control valve. The $O_2$ probe was maintained at a constant temperature by mounting it in a small jacketed receiver. Oxygen was metered into the reactor through a 0-2 l/min Sierra mass flow controller. The outputs from both the $O_2$ meter and the mass flow controller were fed to the Mac+Workbench™. Flow set point to the mass flow controller came from the Mac+Workbench™. Temperature, $O_2$ flow rate, % $O_2$ and d% $O_2$/dt were charted on the computer and the data recorded every minute. The results are shown graphically in FIG. 2.

When all of the PMIDA became oxidized, 6:40 after the start of the oxygen, the $O_2$ concentration increased rapidly. By monitoring the d% $O_2$/dt, the rate of change in the % $O_2$, this point in the reaction became readily apparent and could be used, if desired, to automatically shut off the flow of oxygen. In this case, when the rate increased to >20% $O_2$/hr., an alarm was turned on and the $O_2$ was turned off manually.

After cooling to room temperature and allowing to stir overnight, a sample of liquor was analyzed by HPLC with the following results:

| | |
|---|---|
| N-methylaminomethylphosphonic acid (MeAMPA) | ≈0.1% |
| aminomethylphosphonic acid (AMPA) | ≈0.1% |
| N-methyl-PMG | 0.4% |
| formaldehyde | 6% |
| PMG | 2.7% |
| formic acid | 3.2% |
| N-formyl-PMG | ≈0.15% |
| PMIDA | trace |

EXAMPLE 6

Example 5 was repeated, but the PMIDA was reduced to half to 80 g to shorten the reaction time by 50%. The oxygen flow was stopped after 160 minutes, or ~80% of the amount of $O_2$ needed to complete the reaction. The liquor was sampled for HPLC analysis. The formaldehyde concentration was 2.1% (but would have been ~4.2% if the charge of PMIDA had remained at 160 g as in Example 5). Unoxidized PMIDA was seen but not quantified.

The pressure was vented to atmospheric and 50% $H_2O_2$ slowly pumped into the reaction mixture while maintaining the vent gas % $O_2$ at $\leq 10\%$ by adjusting the $H_2O_2$ pumping rate. After a 15.5 g had been added, no unreacted PMIDA was found in the liquor and the formaldehyde concentration was reduced to 1.2%.

More 50% $H_2O_2$ was added very slowly while maintaining the temperature at 60° C. After a total of 27.3 g had been added, the liquor was sampled and analyzed by HPLC. The formaldehyde concentration was reduced to 0.17% and the AMPA had increased from nil to ~0.6% and the MeAMPA to ~0.4%.

What is claimed is:

1. A process for preparing N-phosphonomethyl glycine or salts thereof which comprises:
   (a) oxidizing N-phosphonomethyl-iminodiacetic acid or a salt thereof in a vessel with an oxidizing agent consisting essentially of hydrogen peroxide in the presence of activated carbon at a temperature effective for producing said N-phosphonomethyl glycine or salts thereof,
   (b) venting the gaseous reaction products from said vessel; and
   (c) regulating the amount of said oxidizing agent allowed to react with said N-phosphonomethyliminodiacetic acid at any given time based upon the concentration of oxygen in said gaseous reaction products.

2. The process of claim 1, wherein the amount of said oxidizing agent allowed to react with said N-phosphonomethyliminodiacetic acid is regulated so that said concentration of oxygen in said gaseous reaction products does not exceed about 50%.

3. The process of claim 1, wherein the amount of said oxidizing agent allowed to react with said N-phosphonomethyliminodiacetic acid is regulated so that said concentration of oxygen in said gaseous reaction products does not exceed about 20%.

4. The process of claim 1, wherein the amount of said oxidizing agent allowed to react with said N-phosphonomethyliminodiacetic acid is regulated so that said concentration of oxygen in said gaseous reaction products does not exceed about 10%.

5. The process of claim 1, wherein the amount of said oxidizing agent allowed to react with said N-phosphonomethyliminodiacetic acid is regulated so that said concentration of oxygen in said gaseous reaction products does not exceed about 3%.

6. The process of claim 1 wherein the reaction is carried out at a temperature of from about 20° to about 150° C.

7. The process of claim 1 wherein the reaction is carried out at a temperature of from about 50° to about 65° C.

8. The process of claim 1 wherein said activated carbon has a specific surface area of from about 100 to about 2000 $m^2/g$.

9. The process of claim 1 wherein said activated carbon has a specific surface area of from about 400 to about 1600 $m^2/g$.

10. The process of claim 1 wherein the initial ratio of activated carbon to phosphonomethyliminodiacetic acid is from about 0.01 to about 10.

11. The process of claim 1 wherein the initial ratio of activated carbon to phosphonomethyliminodiacetic acid is from about 0.1 to about 1.

12. The process of claim 1 wherein the initial ratio of activated carbon to phosphonomethyliminodiacetic acid is from about 0.2 to about 0.4.

13. The process of claim 1, wherein the amount of oxidizing agent allowed to react with said N-phosphonomethyliminodiacetic acid is decreased to zero when said concentration of oxygen in said gaseous reaction products increases by a rate exceeding 20% per hour.

14. A process for preparing N-phosphonomethyl glycine or salts thereof which comprises:
   (a) feeding N-phosphonomethyl-iminodiacetic acid or a salt thereof into a vessel;
   (b) oxidizing said N-phosphonomethyl-iminodiacetic acid with an oxygen-containing gas in the presence of activated carbon at a temperature effective for producing said N-phosphonomethyl glycine or salts thereof;
   (c) venting the gaseous reaction products from said vessel; and
   (d) ceasing said oxidation when the concentration of oxygen in said gaseous reaction products increases at a predetermined rate.

15. A process for preparing N-phosphonomethyl glycine or salts thereof which comprises:
   (a) feeding N-phosphonomethyl-iminodiacetic acid or a salt thereof into a vessel;
   (b) oxidizing a portion of said N-phosphonomethyl-iminodiacetic acid or salt thereof with an oxygen-containing gas in the presence of activated carbon at a temperature effective for producing said N-phosphonomethyl glycine or salts thereof;
   (c) venting the gaseous reaction products from said vessel;
   (d) oxidizing substantially all of the remaining N-phosphonomethyl-iminodiacetic acid or salt thereof with hydrogen peroxide; and
   (e) ceasing said oxidation reaction when concentration of oxygen in said gaseous reaction products increases at a predetermined rate.

16. The process of claim 1, further comprising monitoring the concentration of oxygen in said gaseous reaction products.

17. The process of claim 14, further comprising monitoring the concentration of oxygen in said gaseous reaction products.

18. The process of claim 14, wherein said predetermined rate is a rate exceeding 20% per hour.

19. The process of claim 15, further comprising monitoring the concentration of oxygen in said gaseous reaction products.

20. The process of claim 15, wherein said predetermined rate is a rate exceeding 20% per hour.

21. The process of claim 15, wherein said portion of N-phosphonomethyl-iminodiacetic acid or salt oxidized with an oxygen containing gas is 70–80% of the amount of said N-phosphonomethyl-iminodiacetic acid or salt fed into said vessel.

22. A process for preparing N-phosphonomethyl glycine or salts thereof which comprises oxidizing N-phosphonomethyl-iminodiacetic acid or a salt thereof in a vessel with an oxidizing agent consisting essentially of hydrogen peroxide in the presence of activated carbon at a temperature effective for producing said N-phosphonomethyl glycine or salts thereof.

* * * * *